US006670614B1

(12) United States Patent
Plut et al.

(10) Patent No.: US 6,670,614 B1
(45) Date of Patent: Dec. 30, 2003

(54) VOLUME CONE BEAM ACQUISITION ON A NUCLEAR SPECT SYSTEM USING A DIGITAL FLAT PANEL

(76) Inventors: Leonard F. Plut, 8411 Hendricks Rd., Mentor, OH (US) 44060-2559; Gerhard P. Roos, 17166 Sunset Dr., Bainbridge, OH (US) 44023; Andrew J. Ivan, Jr., 10010 Pirates Trail, Aurora, OH (US) 44202; Frank C. Valentino, 6957 Kingswood Dr., Solon, OH (US) 44139

(*) Notice: Subject to any disclaimer, the term of this patent is extended or adjusted under 35 U.S.C. 154(b) by 0 days.

(21) Appl. No.: 09/873,012

(22) Filed: Jun. 1, 2001

(51) Int. Cl.[7] .............................................. G01T 1/166
(52) U.S. Cl. .............................. 250/363.04; 250/363.1; 250/370.08; 250/370.09; 250/363.01; 250/363.02
(58) Field of Search ...................... 250/363.04, 363.01, 250/363.02, 363.03, 363.05, 363.08, 369, 363.1, 370.08, 370.09, 370.11, 362; 378/4, 5, 13, 14, 21, 22

(56) References Cited

U.S. PATENT DOCUMENTS

| | | | |
|---|---|---|---|
| 2,818,510 A | 12/1957 | Verse ........................... 250/91 |
| 4,150,297 A | 4/1979 | Borggren ..................... 250/490 |
| 5,055,687 A * | 10/1991 | Ichihara ..................... 250/363.09 |
| 5,327,474 A | 7/1994 | Inoue et al. .................... 378/20 |
| 5,376,795 A * | 12/1994 | Hasegawa et al. ...... 250/363.04 |
| 5,391,877 A | 2/1995 | Marks .................... 250/363.04 |
| 5,461,232 A * | 10/1995 | McCandless et al. .. 250/363.04 |
| 6,031,888 A | 2/2000 | Ivan et al. ..................... 378/20 |
| 6,041,097 A | 3/2000 | Roos et al. ..................... 378/62 |
| 6,075,837 A | 6/2000 | Roos et al. ................. 378/98.2 |
| 6,092,928 A | 7/2000 | Mattson et al. ............. 378/205 |
| 6,149,592 A | 11/2000 | Yanof et al. ................. 600/427 |
| 6,171,243 B1 | 1/2001 | Gagnon et al. ............. 600/431 |
| 6,236,708 B1 * | 5/2001 | Lin et al. ....................... 378/22 |
| 6,318,892 B1 * | 11/2001 | Suzuki et al. ............... 378/197 |
| 6,490,476 B1 * | 12/2002 | Townsend et al. .......... 600/427 |

FOREIGN PATENT DOCUMENTS

| WO | WO 91/00048 | 1/1991 |
|---|---|---|
| WO | WO 9100048 A2 * | 1/1991 |

OTHER PUBLICATIONS

LaCroix, et al., "Investigation of the Use of X–ray CT Images For Attenuation Compensation in SPECT", IEEE Trans. on Nucl. Sci. V. 41, N. 6 Dec. 1994, pp. 2793–2799.
Hasegawa, et al., "Object–Specific Attenuation Correction of SPECT with Correlated Dual–Energy X–Ray CT", IEEE Trans. on Nucl. Sci. V. 40, N. 4, Aug. 1993 pp. 1242–1252.
Swissray Medical Systems, Inc. Advertisement—Medical Imaging Sep. 1997 "Digital AddOn—Multi–System for General Radiography".
Fischer Imaging Corporation Product Data Sheet—0591 "CSP—Ceiling Suspended Imaging System".
Picker International, Inc. Product Data Sheet—1994 "Orbitor HF Mobile C–Arms".

* cited by examiner

*Primary Examiner*—Albert Gagliardi
(74) *Attorney, Agent, or Firm*—Fay, Sharpe, Fagan, Minnich & McKee, LLP (57) ABSTRACT

A diagnostic imaging system includes a rotating gantry (16; 216) which defines a subject receiving aperture (18; 218). A rotatable source of high energy penetrating radiation (20; 220) and a corresponding two-dimensional flat panel x-ray detector (26; 226) are disposed across the subject receiving aperture (18; 218). A plurality of nuclear detector heads (40*a*, 40*b*; 240*a*–240*c*) are movably attached to the rotating gantry (16; 216) in order to detect radiation emitted by a radiopharmaceutical injected into the subject (12; 212). Each of the nuclear detector heads (40*a*, 40*b*; 240*a*–240*c*) within the system includes a variable radiation shield (42*a*, 42*b*) disposed adjacent a radiation receiving face on the detector head. The diagnostic imaging system may be operated in a fluoroscopic/radiographic mode in which an isocentric x-ray beam strikes the center of the detector surface or in a volume imaging mode.

22 Claims, 6 Drawing Sheets

VOLUME CONE BEAM ACQUISITION ON A NUCLEAR SPECT SYSTEM USING A DIGITAL FLAT PANEL

BACKGROUND OF THE INVENTION

The present invention relates to the art of medical diagnostic imaging. It finds particular application in conjunction with combined computed tomography (CT) and positron emission tomography (PET) scanners and will be described with particular reference thereto. However, it is to be appreciated that the present invention is also applicable to multi-headed single photon emission computed tomography (SPECT) scanners as well as other combined diagnostic modes.

Diagnostic nuclear imaging is used to study a radionuclide distribution in a subject. Typically, one or more radiopharmaceuticals or radioisotopes are injected into a subject. The radiopharmaceuticals are commonly injected into the subject's bloodstream for imaging the circulatory system or for imaging specific organs, which absorb the injected radiopharmaceuticals. Scintillation crystal camera detector heads are placed adjacent to a surface of the subject to monitor and record emitted radiation. Typically, the detector heads are rotated or indexed around the subject in order to monitor the emitted radiation from a plurality of directions. The detected radiation data is then reconstructed into a three-dimensional image representation of the radiopharmaceutical distribution within the subject.

One of the problems with both PET and SPECT imaging techniques is that photon absorption and scatter by portions of the subject or subject support between the emitting radionuclide and the detector heads distort the resultant image. In order to obtain more accurate SPECT and PET radiation attenuation measurements, a direct transmission radiation measurement is made using transmission computed tomography techniques. In the past, transmission radiation data was commonly acquired by placing a radioactive isotope line or point source opposite to a detector head, enabling the detector head to collect transmission data concurrently with the other two detector heads collecting emission data. This transmission data is then reconstructed into an image representation using conventional tomography algorithms. From this data, regional radiation attenuation properties of the subject, which are derived from the transmission computer tomography images, are used to correct or compensate for radiation attenuation in the emission data.

One PET scanning technique involves the injection of a radioisotope, which is selectively absorbed by tumors or other tissues of interest. The resulting PET images provide an accurate depiction of a location of the tumors in space. However, because only the radioactive isotope is imaged, the PET images provide no correlation between the image and the surrounding tissue. In order to coordinate the tumors with location within the patient, the same region of the subject is scanned with both the PET scanner and a computed tomography (CT) scanner. In the past, the PET and CT scanners were permanently mounted in a displaced relationship to each other. A patient was moved from one apparatus to the next. However, due to potential patient movement and/or repositioning between the CT scanner and the nuclear camera, this technique provided uncertainty in the alignment of the PET and CT images.

To eliminate the alignment problems associated with physically displaced imaging systems, it would be advantageous to mount the CT and nuclear imaging systems to a common gantry. One prior art system includes a two-headed nuclear system and a low power CT system mounted back to back within a single housing with a common patient support. The CT scanner includes a single row of CT or x-ray detectors and a low power x-ray tube which are axially displaced from the nuclear camera heads. The region of interest of the subject was shifted to the CT scanning region before or after the PET scan to acquire anatomical mapping data. Due to the single row of CT detectors, the prior art system is limited to acquiring a ten millimeter slice of reconstructed data. Therefore, the system is required to make many scans in order to provide enough slices of reconstructed data for significant volume coverage. Additional scans require added data acquisition and processing delays.

In addition, the prior art system is rather slow, requiring approximately eight minutes to acquire one slice of transmission data. Obtaining a volume image of the region of interest would be even longer—on the order of 25 minutes. Further, the prior art system is not amenable to fluoroscopy and radiography applications during the nuclear study.

The present invention contemplates a new and improved combined diagnostic imaging system which overcomes the above-referenced problems and others.

SUMMARY OF THE INVENTION

In accordance with one aspect of the present invention, a diagnostic imaging system includes a stationary gantry, which defines a subject receiving aperture, and a source of penetrating radiation rotatably mounted on the gantry which transmits transmission radiation through a subject disposed in a subject receiving aperture. The radiation source is mounted for rotation around the stationary gantry subject receiving aperture. A two-dimensional flat panel radiation detector detects radiation transmitted by the source after passage of the radiation through the subject in the subject receiving aperture. At least one nuclear detector head is mounted for rotation around the subject receiving aperture. The detector head detects emission radiation emitted by a radiopharmaceutical injected into the subject. At least one reconstruction processor reconstructs transmission radiation received by the two-dimensional flat panel radiation detector and emission radiation received by the nuclear detector head into volumetric image representations. A fusion processor combines the transmission and emission volumetric image representations together.

In accordance with a more limited aspect of the present invention, the source, the flat panel detector, and the at least one nuclear detector head are mounted to a common rotating gantry for rotation around the subject in a common plane of rotation.

In accordance with another aspect of the present invention, a diagnostic imaging system includes a rotating gantry, which defines a subject receiving aperture. A source of penetrating radiation and a two-dimensional flat panel detector generate a computed tomographic image representation of a subject disposed within the subject receiving aperture. A plurality of nuclear detector heads are rotatably mounted to the gantry. Each detector head has a radiation receiving face and a radiation shielding means for selectively restricting and permitting radiation to strike the radiation receiving face. A method of diagnostic imaging includes shielding the plurality of nuclear detector heads from radiation generated by the source of penetrating radiation. Radiation is transmitted from the radiation source through the subject and toward the corresponding two-dimensional flat panel detector positioned across the subject receiving aperture. The transmitted radiation is reconstructed into a volumetric image representation. A radiopharmaceutical is injected into the subject disposed within the subject receiving aperture. The radiation shielding means are positioned such that radiation emitted by the radiopharmaceutical is receivable by the radiation receiving face. Radiation emitted by the radiopharmaceutical is detected and reconstructed into an emission image representation. The reconstructed volumetric and emission image representations are combined into a combined image representation.

In accordance with a more limited aspect of the present invention, the steps of transmitting radiation from the radiation source and reconstructing the transmitted radiation include laterally shifting the two-dimensional flat panel detector and indexing the source of penetrating radiation through an angle of at least 180° about the subject receiving aperture.

In accordance with another aspect of the present invention, a diagnostic imaging system includes a first gantry, which defines a subject receiving region, and a plurality of nuclear detector heads mounted to the first gantry around the subject receiving region. The detector heads detect emission radiation emitted by a radiopharmaceutical injected into the subject. A source of penetrating radiation is rotatably mounted to one of the first gantry and a second gantry. The source of penetrating radiation transmits transmission radiation through a subject disposed in the subject receiving region. A two-dimensional flat panel radiation detector detects radiation transmitted by the source after passage of the radiation through the subject in the subject receiving region. At least one reconstruction processor reconstructs transmission radiation received by the two-dimensional flat panel radiation detector and emission radiation received by the plurality of nuclear detector heads into volumetric image representations. A fusion processor combines the transmission and emission volumetric image representations together.

In accordance with a more limited aspect of the present invention, the second gantry onto which the source of penetrating radiation and the two-dimensional flat panel radiation detector are mounted is axially offset from the first gantry.

In accordance with a more limited aspect of the present invention, the plurality of nuclear detector heads include at least three pairs of nuclear detector heads spaced opposite each other across the subject receiving aperture for coincidence detection.

In accordance with a more limited aspect of the present invention, a diagnostic imaging system further includes a radiation shielding means connected to each nuclear detector head for shielding the nuclear detector head from high energy radiation originating from the source of penetrating radiation.

In accordance with a more limited aspect of the present invention, a diagnostic imaging system further includes a radiation shielding means connected to each nuclear detector head for shielding the nuclear detector head from transmission radiation originating from the source of penetrating radiation.

One advantage of the present invention is that it facilitates combined CT/PET diagnostic imaging.

Another advantage of the present invention resides in time-efficient full volume three-dimensional CT data acquisition.

Another advantage of the present invention resides in the ability to perform fluoroscopy during a nuclear study.

Another advantage of the present invention resides in the ability to perform radiography during a nuclear study.

Another advantage of the present invention resides in use of a flat panel detector for use in volume data acquisition and anatomical mapping.

Another advantage resides in the ability to interleave CT and nuclear data collection.

Other benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
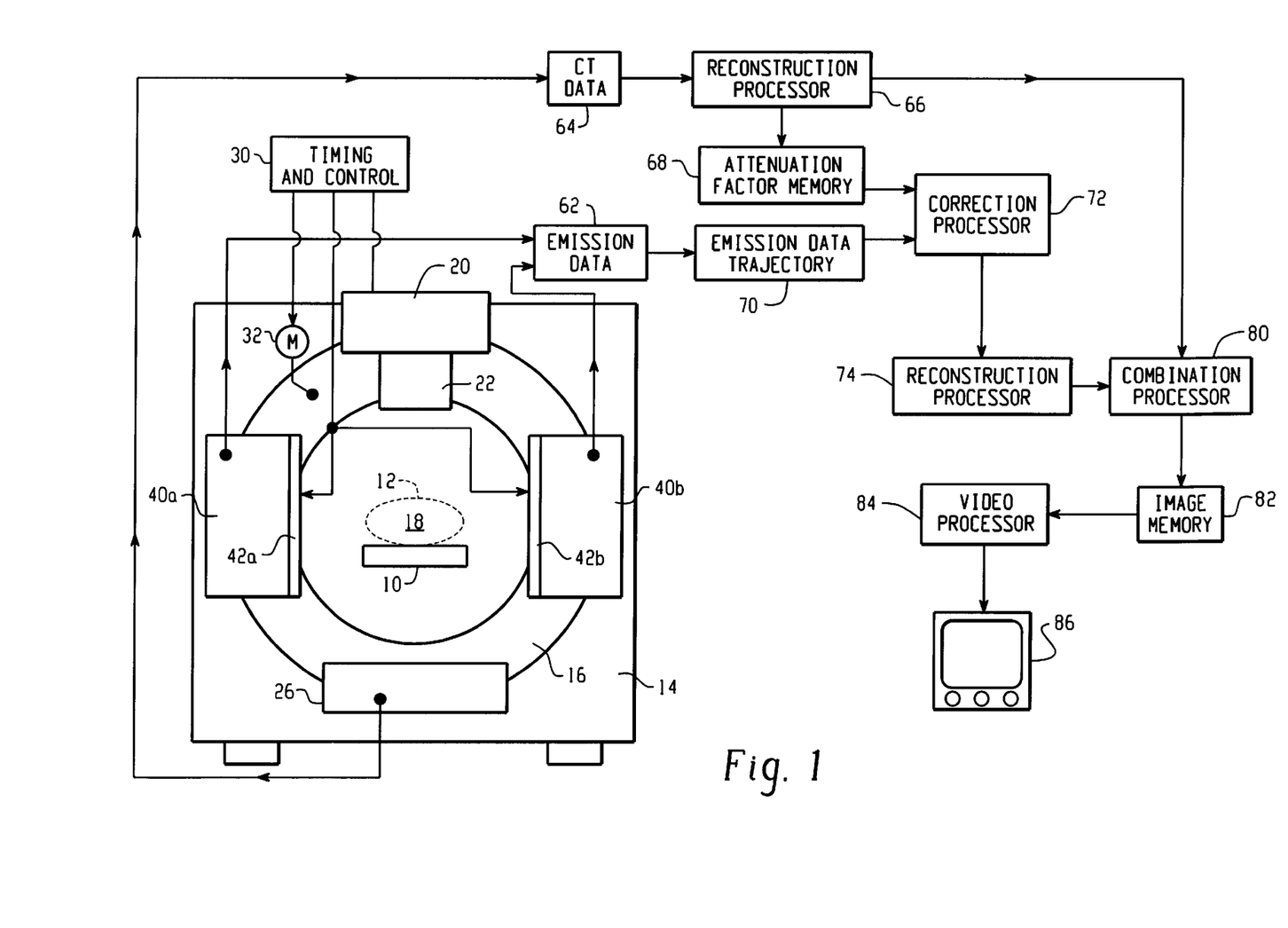
FIG. 1 is a diagrammatic illustration of a combined positron emission tomography (PET)/computerized tomographic (CT) diagnostic system in accordance with the present invention.

With reference to FIG. 1, a diagnostic imaging apparatus includes a subject support 10, such as a table or couch, which supports a subject 12 being examined and/or imaged. The subject 12 is injected with one or more radiopharmaceuticals or radioisotopes, such that emission radiation is emitted therefrom. The subject support 10 is selectively height adjustable so as to center the subject at a desired height. A first or stationary gantry 14 rotatably supports at least one rotating gantry 16. The rotating gantry 16 defines a subject receiving aperture 18. The subject support 10 is advanced and/or retracted to achieve the desired positioning of the subject 12 within the subject receiving aperture 18.

An x-ray tube assembly 20 mounted on the rotating gantry 16 projects one or more beams of radiation through the subject receiving aperture 18. A collimator 22 collimates the radiation into a selected pattern, such as one or more substantially parallel fan beams of selected thickness, a wedge or cone beam of diverging rays, or other selected beam cross-section. An x-ray detector 26, preferably a two-dimensional, flat panel x-ray detector, is rotatably disposed on the rotating gantry across the subject receiving aperture 18 from the x-ray tube 20. More specifically to the preferred embodiment, the flat panel x-ray detector 26 includes a grid of amorphous silicon elements on the order of a millimeter square, with the overall detector being on the order of 16 cm×20 cm. However, it is to be appreciated that two-dimensional flat panel detectors of varying dimensions may be employed. Each element of the amorphous silicon detector integrates the intensity of received radiation over a sampling period and generates an electronic data value indicative of the intensity of received radiation. Typically, all of the elements are read out concurrently or in close temporal proximity to generate a view representative of x-ray intensity variation, which, in turn, is indicative of a projection of radiation opacity of the region of interest taken in the direction of the x-ray beam.

A timing and control circuit 30 controls a drive motor 32 to index the x-ray tube to each of a plurality of pre-selected angular positions around the subject 12. At each step, the timing and control circuit 30 causes an x-ray tube power supply (not shown) to pulse the x-ray tube 20 at radiographic energy levels in a radiographic mode of operation, and fluoroscopic energy levels in a fluoroscopic mode of operation. The x-ray tube 20 sends a pulse of x-rays for a limited duration through the subject striking the flat panel detector 26. Due to the low fluoroscopic energy levels in the fluoroscopic mode of operation, each cell of the two-dimensional, flat panel detector 26 integrates received radiation over the duration of the pulse.

At least two nuclear detector heads 40a, 40b are movably mounted to a rotating gantry, shown in FIG. 1 as the same rotating gantry 16 as the x-ray tube assembly. Mounting the x-ray tube assembly and the nuclear detector heads permits the region of interest to be imaged by both modalities without shifting the patient. Mounting the x-ray sub-system and the nuclear detector heads to separate offset gantries simplifies achieving the different rotational speed at with which CT and nuclear cameras typically rotate. The detector heads 40a, 40b are radially adjustable to vary their spacing. In SPECT cameras, separate translation devices (not shown) translate the heads laterally and circumferentially.

Figure 2:
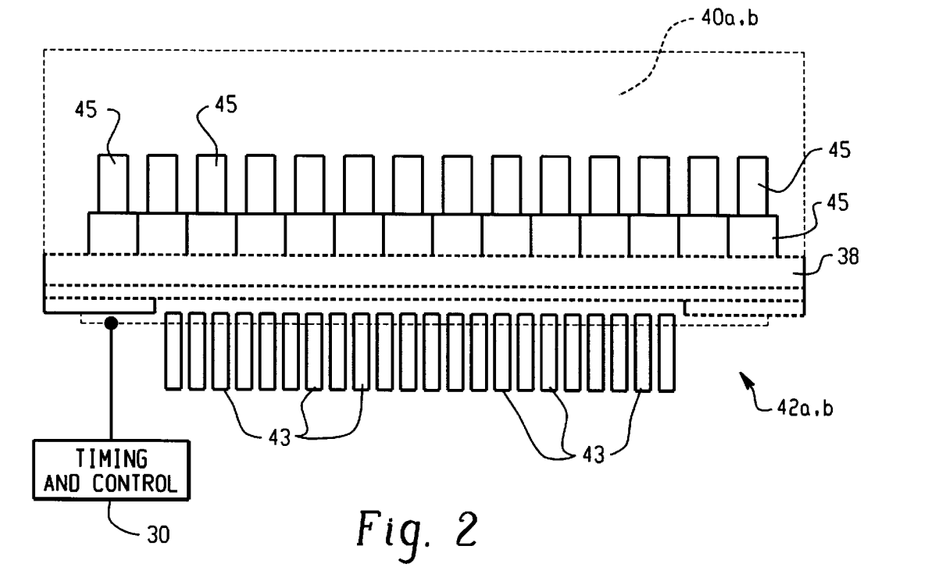
FIG. 2 is a diagrammatic illustration of a nuclear detector head employing a variable axial radiation shield in an open configuration in accordance with the present invention.
Figure 3:
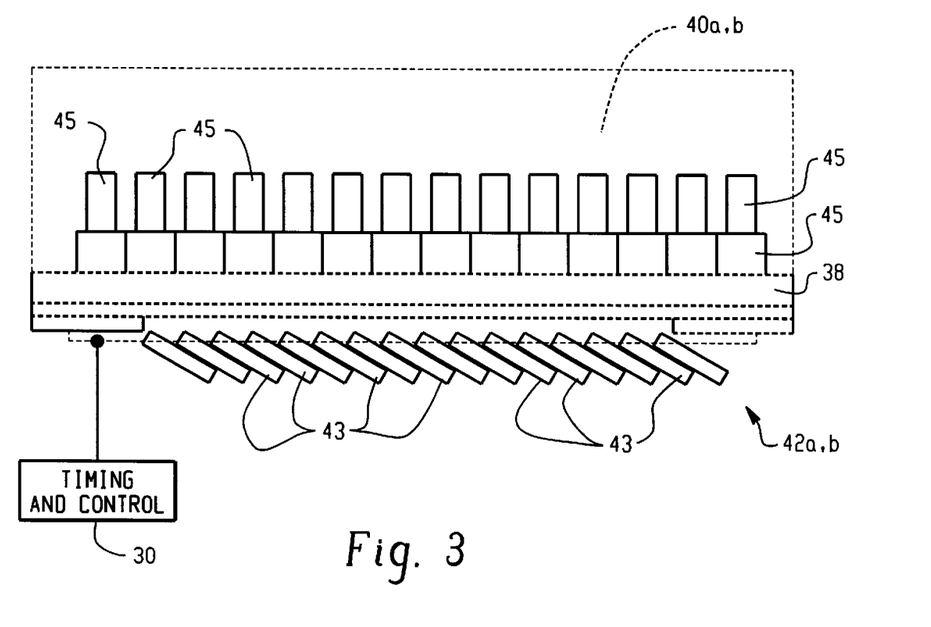
FIG. 3 is a diagrammatic illustration of a nuclear detector head employing a variable axial radiation shield in a closed configuration in accordance with the present invention.

With reference to FIGS. 2 and 3, each of the nuclear detector heads 40a, 40b has a radiation receiving face facing the subject receiving aperture 18. Each nuclear detector head includes a scintillation crystal 38, such as a large, doped sodium iodide crystal, which emits a flash of light or photons in response to incident radiation. The nuclear detector heads 40a, 40b include variable radiation shielding means 42a, 42b which are adjustably mounted on the radiation receiving faces of the detector heads. The variable radiation shielding means 42a, 42b restrict the nuclear detector heads from either receiving radiation not traveling along selected rays or completely shield the detector heads from receiving any radiation.

In one embodiment, illustrated in FIGS. 2 and 3, the radiation shield 42a, 42b includes a plurality of pivoted slats 43. When perpendicular to the face of the detector heads, as illustrated in FIG. 2, the slats 43 permit radiation to pass between each other. When rotated generally parallel to the face of the detector heads, as illustrated in FIG. 3, the slats 43 prevent radiation from striking the faces. In another embodiment, the shield is a flexible or articulated cover which is unrolled across the face of the detector heads. Sliding, pivoting, and other covers are also contemplated. The timing and control circuit 30 moves the shields to their radiation blocking position prior to each actuation of the x-ray tube.

An array of photomultiplier tubes 45, or other opto-electrical elements, receive the light from the scintillation crystal and convert it into electrical signals. A resolver circuit resolves the x, y-coordinates of each flash of light and the corresponding energy of the incident radiation. That is to say, radiation strikes the scintillation crystal causing the scintillation crystal to scintillate, i.e., emit light photons in response to the incident radiation. The photons are received by the photomultiplier tubes and the relative outputs of the photomultiplier tubes are processed and corrected to generate an output signal indicative of (i) a position coordinate on the detector head at which each radiation event is received, and (ii) an energy associated with each event.

In SPECT imaging applications, a projection image representation is defined by the radiation data received at each coordinate. In PET imaging applications, the detector head outputs are monitored for coincident radiation. From the position and orientation of the heads and the location on each head at which the coincident radiation was received, a ray between the peak detection points is calculated. This ray defines a line along which the radiation event occurred. The emission radiation data is then reconstructed into a volumetric image representation of the region of interest.

Figure 4:
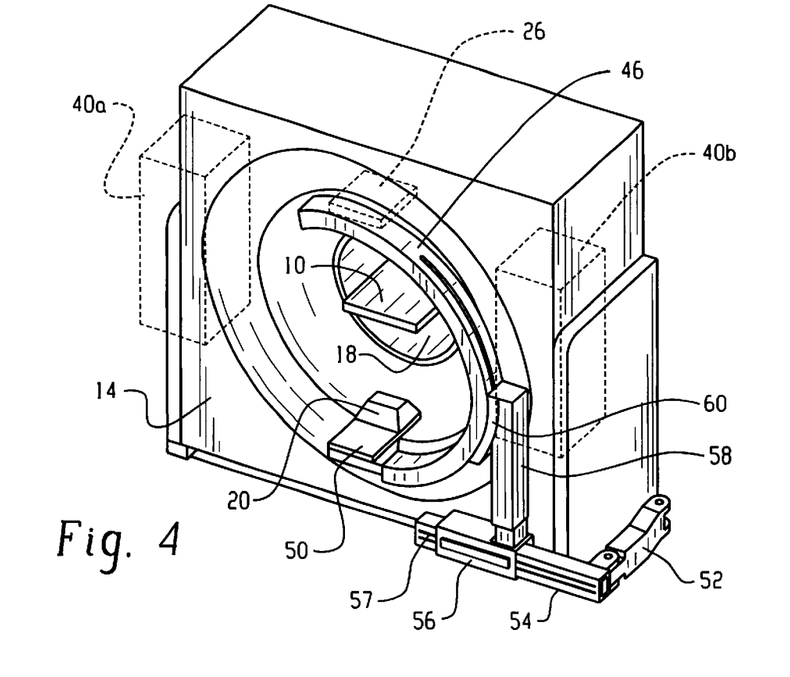
FIG. 4 is a perspective view of the combined PET/CT diagnostic imaging system with a C-arm shown in an operating position in accordance with the present invention.
Figure 5:
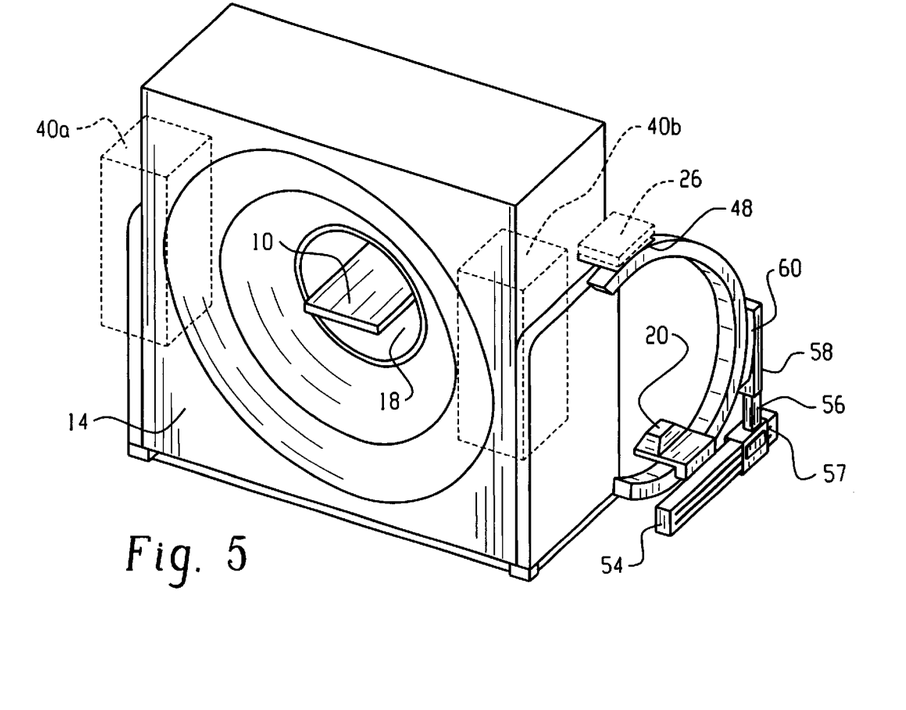
FIG. 5 is a perspective view of the combined PET/CT diagnostic system with a C-arm in the stored position in accordance with the present invention.

With reference to FIG. 4 and FIG. 5 and continuing reference to FIG. 1, an alternate embodiment of the present invention includes a support member for supporting at least one of the x-ray source 20 and the two-dimensional flat panel detector 26. The support member facilitates movement of the source of penetrating radiation 20 and the two-dimensional flat panel detector 26 at a variety of positions around the subject receiving aperture 18. In one embodiment, the support member is a C-arm 46 in which the x-ray tube 20 is secured proximate a first end of the C-arm 46 via a cantilevered support bracket 48. Likewise, the opposing two-dimensional flat panel detector 26 is secured proximate a second end of the C-arm 46 via a cantilevered support bracket 50.

The support structure includes a first link or support arm 52 having one end pivotally secured to the stationary gantry 14 and the other end pivotally secured to a second support arm 54. A first upright support arm 56 is movably secured to the second support arm 54 for substantial horizontal movement along a track 58 associated with the second arm 54. A second upright support arm is movably secured to the first upright support arm 56 for substantial vertical movement along a common longitudinal axis of the upright support arms. The C-arm 46 is rotatably supported by a bearing assembly associated with the second upright support arm 58, which permits the x-ray source 20 and two-dimensional flat panel detector 26 to rotate about a geometric center of the C-arm through an arc of at least 180°.

The support member may be conveniently stored or parked along the side of the gantry when not in use, as shown in FIG. 5, and when needed, positioned in front of the gantry with the x-ray source positioned above or below the patient support member, as shown in FIG. 4. As is described more fully below, the two-dimensional flat panel detector may be secured to a flip-mount structure in which the flat panel detector is positioned in a fluoroscopic/radiographic mode or a volume imaging mode or folded away from the subject receiving aperture.

Referring again to FIG. 1, when emission radiation from the subject and transmission radiation from the x-ray source are received by the nuclear detector heads 40a, 40b and x-ray detector 26, respectively, emission projection data and transmission projection data are generated. The emission data often contains inaccuracies caused by varying absorption characteristics of the subject's anatomy. The data is stored in either an emission data memory 62 or a CT data memory 64. A first reconstruction processor 66 reconstructs the collected transmission data, using an appropriate CT reconstruction algorithm, such as a volume cone beam reconstruction, into a transmission image representation. From the reconstructed transmission image representation, an array of attenuation factors is determined and stored in an attenuation factor memory 68. Each voxel value stored in the attenuation factor memory 68 is indicative of attenuation of radiation by tissue in a corresponding volume within the subject 12.

An emission data trajectory processor 70 determines the trajectory of each emission data ray relative to the volumetric image representation in the attenuation factor memory and causes the attenuation values along the ray to be retrieved. An emission data correction processor 72 corrects the emission data in accordance with the attenuation factors determined from the CT data. More specifically, for each ray along which emission data is received, the emission data trajectory processor 70 calculates a corresponding ray through the attenuation factor array stored in the attenuation factor memory 68. Each ray of the emission data is then weighted or corrected by the emission data correction processor 72 in accordance with the attenuation factors.

The corrected emission data is reconstructed by a second reconstruction processor 74 in order to generate a three-dimensional emission image representation. The three-dimensional emission image representation is than combined or fused with the CT volumetric image representation by way of a combination processor 80. It is to be appreciated that the combined or fused image representation provides functional anatomical mapping. The fused or combined image representation is stored in a volumetric image memory 82. An image processor 84 withdraws selected portions of the data from the image memory 82 to generate corresponding human-readable displays on a monitor 86. Typical displays include reprojections, selected slices or planes, surface renderings, and the like.

Figure 6:
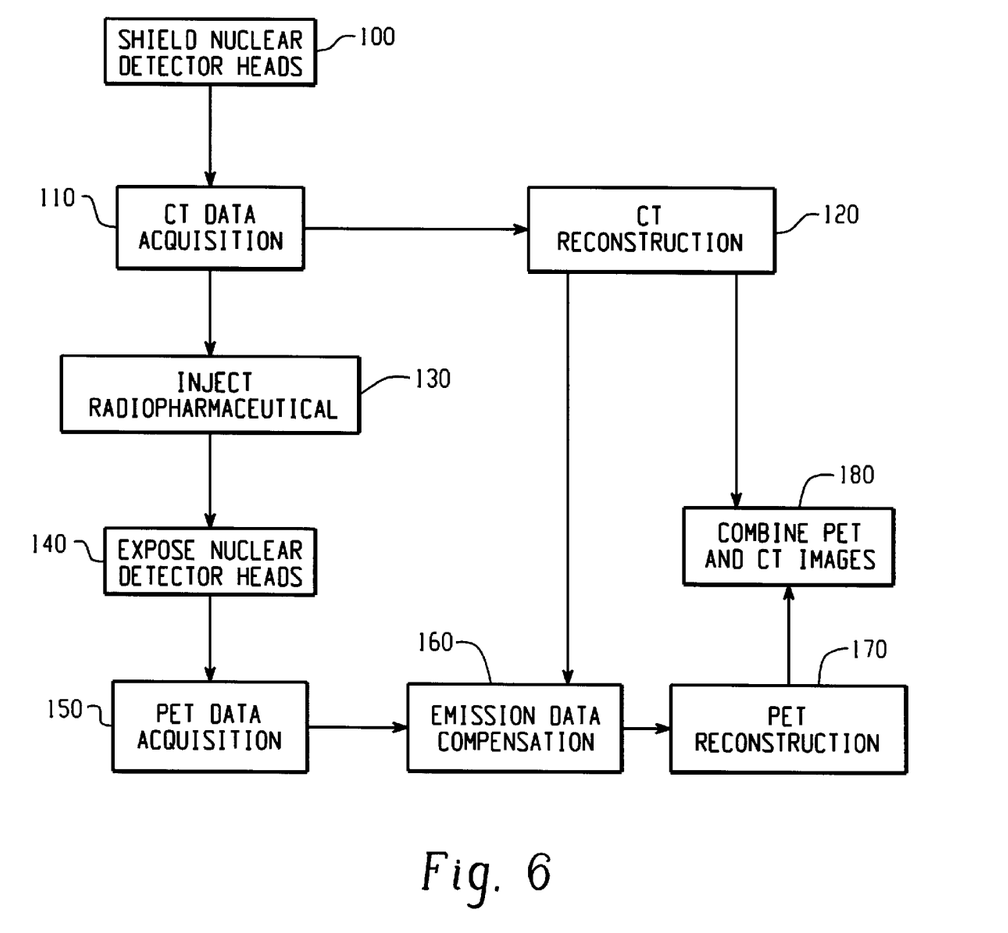
FIG. 6 is a flow chart illustrating a method of diagnostic imaging in accordance with the present invention.

With reference to FIG. 6 and continuing reference to FIG. 1, a method of diagnostic imaging illustrated using the diagnostic imaging system of FIG. 1 is provided. More particularly, the diagnostic imaging method relates to a combined PET/CT scanning technique involving the injection of a radiopharmaceutical, which is selectively absorbed by tumors or other tissues of interest. It is to be appreciated that the resultant PET image provides an accurate depiction of the location of the tumor or other tissue of interest in space. However, because only the radiopharmaceutical is imaged, the PET image provides little, if any, correlation between the image and the surrounding tissue. In order to coordinate the tumors or other regions of interest with surrounding tissue, the same region of the subject is scanned in a CT mode as well.

Initially, the nuclear detector heads 40a, 40b are shielded 100 via the variable radiation shielding means 42a, 42b. In one embodiment, the variable radiation shielding means include a plurality of substantially parallel radiation opaque vanes, which are pivoted or otherwise translated in one of a radiation shielding mode or a radiation exposure mode. Shielding the nuclear detector heads protects each scintillator from transmission radiation events that originate from the x-ray source or other source of penetrating radiation.

Once the variable radiation shielding means is in the radiation shielding mode, a CT data acquisition is performed 110. More particularly, x-ray radiation is transmitted from the x-ray source through the subject and toward the corresponding two-dimensional flat panel x-ray detector positioned across the subject receiving aperture. This x-ray data is then reconstructed 120 using a standard CT reconstruction, such as fan beam reconstruction, a volume cone beam reconstruction or a half-angle reconstruction. If the CT and nuclear heads are axially offset, the patient is indexed axially to shift the region of interest from the CT examination region to the gamma camera examination region. Upon completion of the CT data acquisition 110, the subject is injected 130 with a radiopharmaceutical. If the uptake time is long compared to the CT scan time, the radiopharmaceutical can be injected prior to the CT scan. Once equilibrium is reached with regard to the radiopharmaceutical, the variable radiation shielding means is positioned such that the nuclear detector heads are exposed 140 to incident radiation. In one embodiment, the substantially parallel vanes are opened in a radiation collimating mode. In the radiation collimating mode, non-axial radiation events are blocked or otherwise impeded from reaching the scintillators of the nuclear detector heads.

Once a PET data acquisition sequence is performed 150, the detected emission data is corrected for subject attenuation 160 and reconstructed 170 into a corresponding emission data representation, which is then combined 180 with the CT or transmission image representation to form a combined or fused volumetric image representation.

Alternatively, the CT and PET data can be interleaved. After the patient is injected, the nuclear detectors are shielded and a single CT projection image is taken. The nuclear detectors are exposed and PET data is acquired. The rotating gantry is indexed to another angular orientation and a CT projection and PET data (in either order) are collected. This process is repeated at a plurality of angular positions.

Figure 7:
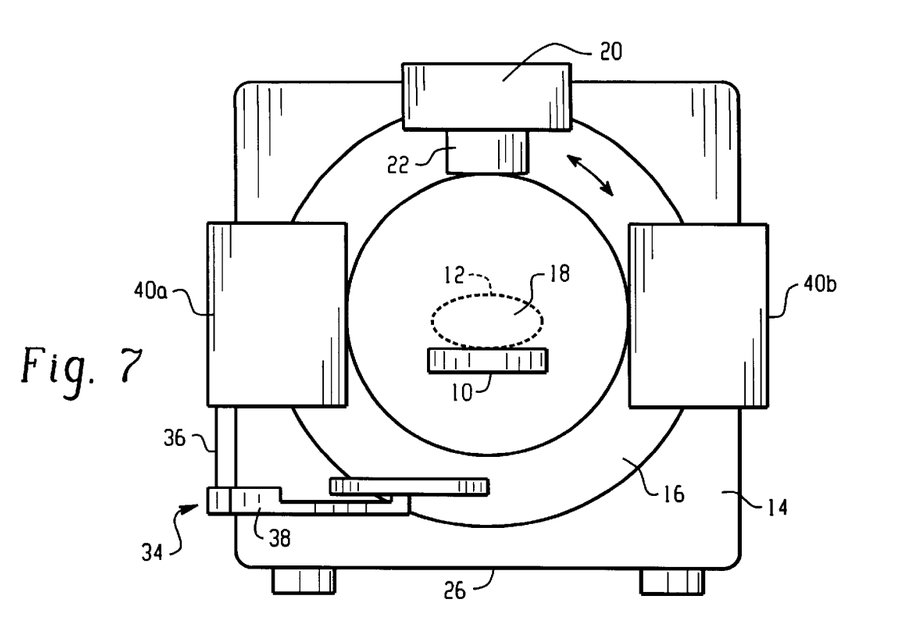
FIGS. 7 and 8 are diagrammatic illustrations of a two-headed embodiment of a combined PET/CT diagnostic system in accordance with the present invention.
Figure 8:
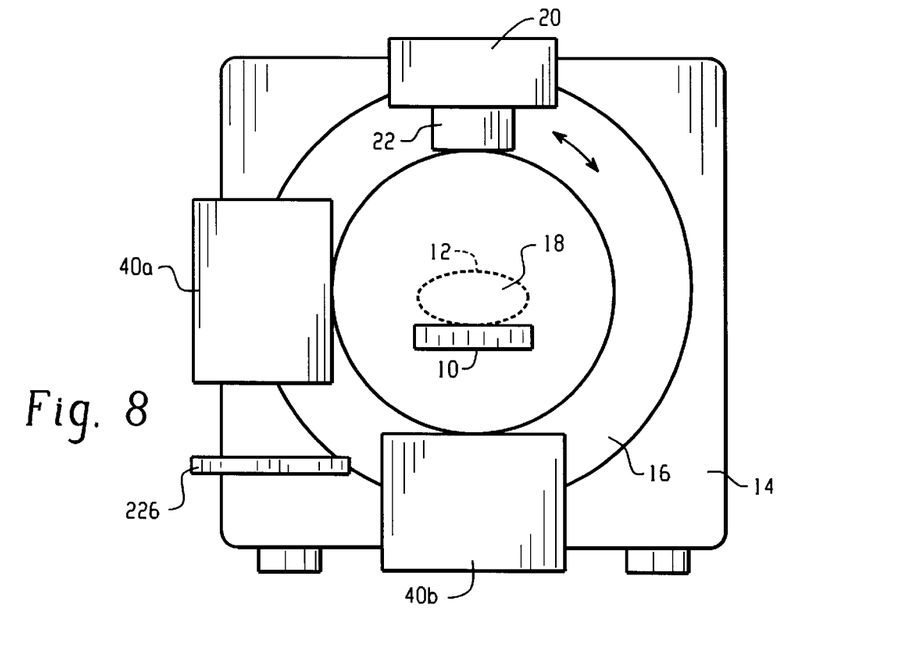

With reference to FIG. 7 and FIG. 8 and continuing reference to FIG. 1, the diagnostic imaging system of the present invention is adaptable to a plurality of imaging modes. For example, FIG. 1 illustrates a two-headed embodiment, that is, two nuclear detector heads 40a, 40b disposed opposite each other across the patient receiving aperture 18. In this embodiment, the two-dimensional flat panel x-ray detector 26 is positioned such that an isocentric x-ray beam falls approximately on the center of the flat panel detector 26 in a fluoroscopic/radiographic imaging mode. As shown in FIG. 7, the two-dimensional flat panel x-ray detector may be shifted laterally, such that an isocentric x-ray cone beam falls approximately on or near one of the shorter edges of the flat panel detector in a volume imaging mode. In this embodiment, the flat panel detector 26 is connected to a flip mount support structure 34. The flip mount support structure 34 consists of a horizontal support member 38 which is pivotally attached to a vertical support member 36, such that the flat panel detector 26 may be translated laterally and/or rotated or folded out of the way of the nuclear detector heads, as shown in FIG. 8. It is to be appreciated that in the volume imaging mode, illustrated in FIG. 7, a 360° scan and offset tomography cone beam reconstruction techniques are employed.

Optionally, a separate sub-system may be included to sense nuclear gantry motion inaccuracies and instability, e.g., vibration, and provide actual x-ray source and detector positional data to the reconstruction processor. This data can then be used to correct a projection image data for such motion and stability prior to reconstruction.

Figure 9:
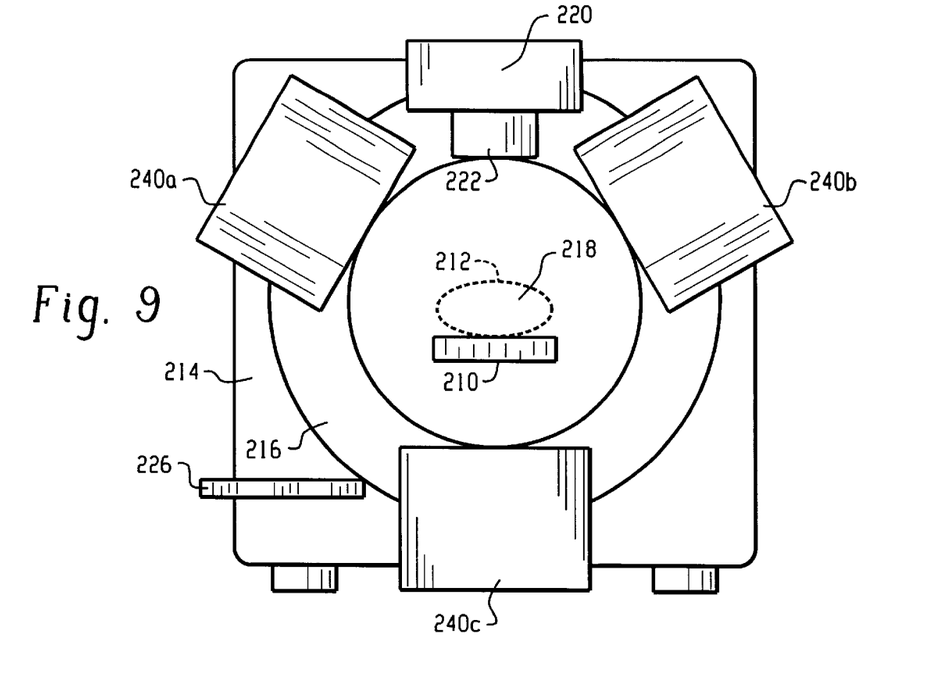
FIGS. 9 and 10 are diagrammatic illustrations of a three-headed embodiment of a combined PET/CT diagnostic system in accordance with the present invention.
Figure 10:
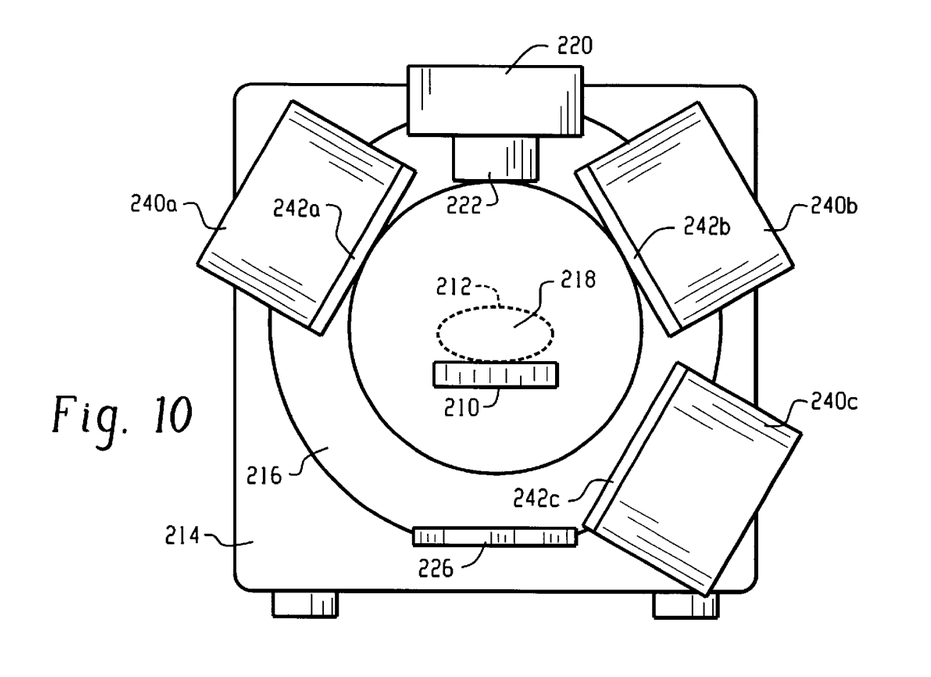

An alternate embodiment of the present invention includes three nuclear detector heads 240a, 240b, 240c disposed around the subject receiver aperture 218. The diagnostic imaging system further includes an x-ray source 220 and a two-dimensional flat panel x-ray detector 226, as illustrated in FIGS. 9 and 10. More particularly, FIG. 9 illustrates a three-headed embodiment with the nuclear detector heads 240a–240c at a 120° configuration with the flat panel x-ray detector 226 moved out of the way. FIG. 10 illustrates the three-headed embodiment with the flat panel detector 226 in the fluoroscopic/radiographic position. Alternately, the two-dimensional flat panel x-ray detector 226 is shifted laterally in front of detector 240c for radiographic/fluoroscopic imaging and shifted away from the detector face for emission imaging.

The present invention also finds application in a multi-head PET system. More particularly, a plurality of nuclear detector heads, e.g., six nuclear detector heads, are mounted symmetrically around a subject receiving aperture. In one embodiment, an x-ray source and optionally a collimator are disposed across the subject receiving aperture from a two-dimensional flat panel x-ray detector. It is to be appreciated that the CT sub-system, that is, the x-ray source and the flat panel detector may be on a separate gantry which is axially offset from the gantry supporting the nuclear detector heads. In this embodiment, the flat panel detector may be positioned in a fluoroscopic/radiographic position such that an isocentric x-ray beam falls approximately on the center of the flat panel detector active area. Alternatively, the flat panel detector may be shifted laterally for operation in a volume imaging mode as is described more fully above.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging system comprising:
   a stationary gantry which defines a subject receiving aperture;
   a source of penetrating radiation rotatably mounted on the gantry, which source transmits transmission radiation through a subject disposed in a subject receiving aperture, the radiation source being mounted for rotation around the stationary gantry subject receiving aperture;
   a two-dimensional flat panel radiation detector for detecting radiation transmitted by the source after passage of the radiation through the subject in the subject receiving aperture;
   at least one nuclear detector head mounted for rotation around the subject receiving aperture, which detector head has a radiation receiving face which detects emission radiation emitted by a radiopharmaceutical injected into the subject;
   a radiation shielding means for selectively restricting and permitting radiation to strike the radiation receiving face;
   a means for positioning the shielding means to shield the radiation receiving facet from radiation generated by the source of transmitted radiation;
   a means for repositioning the radiation shielding means such that radiation emitted by the radiopharmaceutical and traveling only along selectable rays is receivable by the radiation receiving face;
   a first reconstruction processor which reconstructs transmission radiation received by the two-dimensional flat panel radiation detector into a transmission volumetric image representation;
   a second reconstruction processor which reconstructs emission radiation received by the nuclear detector into an emission volumetric image representation; and
   a fusion processor which combines the transmission volumetric image representation and emission volumetric image representation together.

2. The diagnostic imaging system according to claim 1, wherein:
   the source of penetrating radiation and the two-dimensional flat panel radiation detector operate in one of (i) a radiographic mode to generate radiographic image representations and (ii) a fluoroscopic mode to generate fluoroscopic image representations.

3. The diagnostic imaging system according to claim 2, further including:
   a timing and control circuit connected to the source of penetrating radiation, said timing and control circuit pulsing the source of penetrating radiation at fluoroscopic energy levels in the fluoroscopic mode.

4. The diagnostic imaging system according to claim 1, wherein the at least one nuclear detector head includes at least one of:
   a pair of detector heads spaced opposite each other across the subject receiving aperture for coincidence detection;
   a plurality of detector heads symmetrically disposed adjacent the subject receiving aperture for coincidence detection; and
   at least three pairs of detector heads spaced opposite each other across the subject receiving aperture for coincidence detection.

5. The diagnostic imaging system according to claim 1, wherein the source, the flat panel detector, and the at least one nuclear detector head are mounted to a common rotating gantry for rotation around the subject in a common plane of rotation.

6. A diagnostic imaging system including:
   a stationary gantry which defines a subject receiving aperture;
   a source of penetrating radiation rotatably mounted on the gantry which transmits transmission radiation through a subject disposed in a subject receiving aperture, the radiation source being mounted for rotation around the stationary gantry subject receiving aperture;
   a two-dimensional flat panel radiation detector for detecting radiation transmitted by the source after passage of the radiation through the subject in the subject receiving aperture;
   at least one nuclear detector head mounted for rotation around the subject receiving aperture, which detector head detects emission radiation emitted by a radiopharmaceutical injected into the subject and has a plurality of radiation opaque tilting slats adjacent to a radiation receiving face to shield the nuclear detector head from the transmission radiation by moving the plurality of radiation opaque slats between an open configuration in which radiation is received by the nuclear detector head and a closed configuration in which radiation is blocked by the tilting slats from being received by the nuclear detector head;
   a reconstruction processor which reconstructs transmission radiation received by the two-dimensional flat panel radiation detector and emission radiation received by the nuclear detector head into volumetric image representations.

7. The diagnostic imaging system according to claim 6, further comprising;
a support member for supporting at least one of (i) the source of penetrating radiation and (ii) the two-dimensional flat panel radiation detector in one of (i) a stored position remote from the subject receiving aperture and (ii) an operating position proximate the subject receiving aperture.

8. The diagnostic imaging system according to claim 7, wherein the support member includes a C-arm.

9. A diagnostic imaging system including:
a stationary gantry which defines a subject receiving aperture;
a source of penetrating radiation rotatably mounted on the gantry, the radiation source transmitting radiation through a subject disposed in a subject receiving aperture and being mounted for rotation around the stationary gantry subject receiving aperture;
a two-dimensional flat panel radiation detector for detecting radiation transmitted by the source after passage of the radiation through the subject in the subject receiving aperture, two-dimensional flat panel supported by a support member including a horizontal support arm pivotally attached to a vertical support arm such that the two-dimensional flat panel radiation detector may be shifted laterally and folded away from the subject receiving region;
at least one nuclear detector head mounted for rotation around the subject receiving aperture, which detector head has a radiation receiving face which detects emission radiation emitted by a radiopharmaceutical injected into the subject;
a radiation shielding means for selectively restricting and permitting radiation to strike the radiation receiving face;
a means for positioning the shielding means to shield the radiation receiving face from radiation generated by the source of transmitted radiation;
a means for repositioning the radiation shielding means such that radiation emitted by the radiopharmaceutical and traveling only along selectable rays is receivable by the radiation receiving face;
a reconstruction processor which reconstructs transmission radiation received by the two-dimensional flat panel radiation detector into a transmission volumetric image representation and emission radiation received by the nuclear detector head into an emission volumetric image representation; and
a fusion processor which combines the transmission volumetric image representation and emission volumetric image representation together.

10. A diagnostic imaging system including:
a stationary gantry which defines a subject receiving aperture;
a source of penetrating radiation rotatably mounted on the gantry, the radiation source transmitting radiation through a subject disposed in a subject receiving aperture;
a two-dimensional flat panel radiation detector for detecting transmitted radiation after passage of the radiation through the subject in the subject receiving aperture;
at least one nuclear detector head mounted for rotation around the subject receiving aperture, which detector head detects radiation emitted by a radiopharmaceutical injected into the subject at a radiation receiving face;
a radiation shielding means for selectively restricting and permitting radiation to strike the radiation receiving face;
a means for positioning the shielding means to shield the radiation receiving face from radiation generated by the source of transmitted radiation;
a means for repositioning the radiation shielding means such radiation emitted by the radiopharmaceutical and traveling only along selectable rays is receivable by the radiation receiving face;
a first reconstruction processor which reconstructs radiation received by the two-dimensional flat panel radiation into a transmission image representation and determines a plurality of attenuation factors;
an attenuation correction processor for correcting emission data from the nuclear detector head in accordance with the attenuation factors;
a second reconstruction processor which reconstructs the attenuation corrected emission data into an attenuation corrected emission volumetric image representation; and
a fusion Processor which combines the transmission and attenuation corrected emission volumetric image representations together.

11. A diagnostic imaging system comprising:
a first gantry which defines a subject receiving region;
a plurality of nuclear detector heads mounted to the first gantry around the subject receiving region, which detector heads have radiation receiving faces which detect emission radiation emitted by a radiopharmaceutical injected into the subject;
a source of penetrating radiation rotatably mounted to one of the first gantry and a second gantry, which source transmits transmission radiation through a subject disposed in the subject receiving region;
a radiation shielding means for selectively restricting and permitting radiation to strike the radiation receiving faces;
a means for positioning the shielding means to shield the radiation receiving faces from radiation generated by the source of transmitted radiation;
a means for repositioning the radiation shielding means such that radiation emitted by the radiopharmaceutical and traveling only along selectable rays is receivable by the radiation receiving faces;
a two-dimensional flat panel radiation detector for detecting radiation transmitted by the source after passage of the radiation through the subject in the subject receiving region;
at least one reconstruction processor which reconstructs transmission radiation received by the two-dimensional flat panel radiation detector and emission radiation received by the plurality of nuclear detector heads into transmission radiation volumetric image representations and emission radiation volumetric image representations; and
a fusion processor which combines the transmission radiation and emission radiation volumetric image representations together.

12. The diagnostic imaging system according to claim 11, wherein the second gantry onto which the source of penetrating radiation and the two-dimensional flat panel radiation detector are mounted is axially offset from the first gantry.

13. The diagnostic imaging system according to claim 11, wherein the plurality of nuclear detector heads includes:
   at least three pairs of nuclear detector heads spaced opposite each other across the subject receiving aperture for coincidence detection.

14. The diagnostic imaging system according to claim 11, further comprising:
   a means for pulsing the source of penetrating radiation at one of (i) radiographic energy levels and (ii) fluoroscopic energy levels.

15. The diagnostic imaging system according to claim 11, wherein the first gantry rotates and;
   the source and flat panel detector are mounted to the first gantry to rotate around the subject in a common plane with the plurality of nuclear detector heads.

16. A diagnostic imaging system comprising:
   a stationery gantry which defines a subject receiving region;
   a plurality of nuclear detector heads mounted to the stationery gantry around the subject receiving region, which detector heads have radiation receiving faces to detect emission radiation emitted by a radiopharmaceutical injected into the subject;
   a source of penetrating radiation mounted to a rotating gantry, which source transmits transmission radiation through a subject disposed in the subject receiving region;
   a two-dimensional flat panel radiation detector for detecting radiation transmitted by the source after passage of the radiation through the subject in the subject receiving region, movably mounted to the rotating gantry to rotate around the subject in a common plane with the source of penetrating radiation;
   a support member for supporting the two-dimensional flat panel radiation detector for movement between (i) a stored position remote from the subject receiving aperture and (ii) an operating position proximate the subject receiving aperture;
   a radiation shielding means for selectively restricting and permitting radiation to strike the radiation receiving faces;
   a means for positioning the shielding means to shield the radiation receiving faces from radiation generated by the source of transmitted radiation;
   a means for repositioning the radiation shielding means such that radiation emitted by the radiopharmaceutical and traveling only along selectable rays is receivable by the radiation receiving faces;
   at least one reconstruction processor which reconstructs transmission radiation received by the two-dimensional flat panel radiation detector and emission radiation received by the plurality of nuclear detector heads into volumetric image representations; and
   a fusion processor which combines the transmission radiation and emission radiation volumetric image representations together.

17. A diagnostic imaging system having a rotating gantry which defines a subject receiving aperture, a source of transmitted radiation and a corresponding two-dimensional flat panel detector for detecting penetrating radiation which has traversed a subject disposed within the subject receiving aperture, a plurality of nuclear detector heads rotatably mounted to the gantry, said detector heads each having a radiation receiving face and a radiation shielding means for selectively restricting and permitting radiation to strike the radiation receiving face, the system further comprising:
   (a) a means for positioning the shielding means to shield the plurality of nuclear detector heads from radiation generated by the source of transmitted radiation;
   (b) a means for reconstructing the transmitted radiation detected by the flat panel detector into a transmission radiation volumetric image representation;
   (c) a means for repositioning the radiation shielding means such that radiation emitted by the radiopharmaceutical and traveling only along selectable rays is receivable by the radiation receiving face;
   (d) a means for reconstructing the detected emitted radiation into an emission image representation; and
   (e) a means for combining the reconstructed transmission volumetric and emission image representations into a combined image representation.

18. The system according to claim 17, wherein the means for reconstructing the detected emission radiation includes:
   a means for calculating a plurality of attenuation factors from the volumetric image representation; and
   a means for correcting the emission radiation data based on the plurality of calculated attenuation factors.

19. The system according to claim 17, further including:
   a means for laterally shifting the two-dimensional flat panel detector; and
   a means for indexing the source of penetrating radiation through an angle of at least 180E about the subject receiving aperture.

20. The system according to claim 17, further including:
   a means for pulsing the radiation source at one of radiographic fluoroscopic energy levels.

21. The system according to claim 20, wherein the transmitted radiation reconstruction means includes a means for generating a fluoroscopic image representation from the reconstructed transmission radiation.

22. The system according to claim 17, further including:
   a means for positioning the two-dimensional flat panel detector such that an isocentric x-ray beam generated by the source of penetrating radiation falls substantially on a center of the two-dimensional flat panel detector; and
   a means for indexing the source of penetrating radiation about the subject receiving aperture through an angle of at least 180°.

* * * * *